US006433175B1

(12) United States Patent
Adams et al.

(10) Patent No.: US 6,433,175 B1
(45) Date of Patent: Aug. 13, 2002

(54) PYRROLOINDOLES, PYRIDOINDOLES AND AZEPINOINDOLES AS 5-HT$_{2C}$ AGONISTS

(75) Inventors: David Reginald Adams; Jonathan Mark Bentley; Jonathan Richard Anthony Roffey; Richard John Hamlyn; Suneel Gaur; Matthew Alexander James Duncton; James Edward Paul Davidson; Michael John Bickerdike; Ian Anthony Cliffe; Howard Langham Mansell, all of Winnersh (GB)

(73) Assignee: Vernalis Research Limited, Winnersh (GB)

( * ) Notice: Subject to any disclaimer, the term of this patent is extended or adjusted under 35 U.S.C. 154(b) by 0 days.

(21) Appl. No.: 09/763,889
(22) PCT Filed: Sep. 1, 1999
(86) PCT No.: PCT/GB99/02884
§ 371 (c)(1),
(2), (4) Date: Feb. 28, 2001
(87) PCT Pub. No.: WO00/12510
PCT Pub. Date: Mar. 9, 2000

(30) Foreign Application Priority Data

Sep. 1, 1998 (GB) ................................. 9819035

(51) Int. Cl.$^7$ ...................... C07D 487/04; A61K 31/403
(52) U.S. Cl. .................. 546/94; 548/421; 548/428; 514/411; 514/294
(58) Field of Search ............................. 548/428, 421; 546/94; 514/411, 294

(56) References Cited

U.S. PATENT DOCUMENTS

| | | | |
|---|---|---|---|
| 3,250,783 A | | 5/1966 | Remers et al. ............... 260/319 |
| 4,134,894 A | * | 1/1979 | Zinnes et al. .......... 260/326.25 |
| 4,778,812 A | * | 10/1988 | Jirkovsky et al. ............ 514/323 |
| 5,629,427 A | * | 5/1997 | Paterson et al. .......... 546/276.7 |

FOREIGN PATENT DOCUMENTS

| | | |
|---|---|---|
| EP | 0 167 901 | 1/1986 |
| EP | 0 327 307 | 8/1989 |
| WO | 93/18036 | 9/1993 |

OTHER PUBLICATIONS

Bös et al.; "Novel Agonists of 5HT$_{2C}$ Receptors, Synthesis and Biological Evaluation of Substituted 2–(Indol–1–yl)–1–methylethylamines and 2–(Indeno[1,2b] pyrrol–1–yl)–1 methylethylamines. Improved Therapeutics for Obsessive Compulsive Disorder", Journal of Medicinal Chemistry; vol. 40, No. 17; 1997; American Chemical Society; pp. 2762–2769; XP–002124267.

Bös et al.; "Synthesis, Pharmacology and Therapeutic Potential of 10–methoxypyrazino[1,2–a]indoles, Part Agonists at the 5HT$_{2C}$ Receptor"; European Journal of Medicinal Chemistry; vol. 32, No. 3; 1997; Elsevier; pp. 253–261.

Clark et al.; "2–(Quinuclidin–3–yl)pyrido[4,3–b] indol–1–ones and Isoquinolin–1–ones. Potent Conformational Restricted 5–HT$_3$ Receptor Antagonists"; Journal of Medicinal Chemistry; vol. 36, No. 18; 1993; Research pp. 2645–2657; XP–002124268.

* cited by examiner

Primary Examiner—Floyd D. Higel
Assistant Examiner—Kamal Saeed
(74) Attorney, Agent, or Firm—Foley Lardner

(57) ABSTRACT

A chemical compound of formula (I), wherein n is 1, 2 or 3; $R_1$ and $R_2$ are independently selected from hydrogen and alkyl; $R_3$ is alkyl; $R_4$ to $R_7$ are independently selected from hydrogen, halogen, hydroxy, alkyl, aryl, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, or $R_5$ and $R_6$ together form a carbocyclic or heterocyclic ring, and pharmaceutically acceptable salts and prodrugs thereof, and the use thereof in therapy, particularly for the treatment of disorders of the central nervous system; damage to the central nervous system; cardiovascular disorders; gastrointestinal disorders, diabetes insipidus, and sleep apnea, and particularly for the treatment of obesity (1)

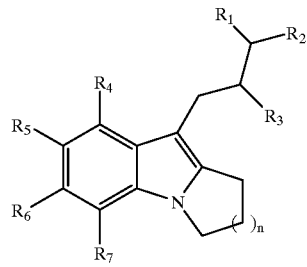

27 Claims, No Drawings

PYRROLOINDOLES, PYRIDOINDOLES AND AZEPINOINDOLES AS 5-HT$_{2C}$ AGONISTS

This application is a 371 PCT/GB99/02884 filed on Sep. 1, 1999.

The present invention relates to pyrroloindole, pyridoindole and azepinoindole derivatives, to processes and intermediates for their preparation, to pharmaceutical compositions containing them and to their medicinal use. The active compounds of the present invention are useful in treating obesity and other disorders.

It has been recognised that obesity is a disease process influenced by environmental factors in which the traditional weight loss methods of dieting and exercise need to be supplemented by therapeutic products (S. Parker, "Obesity: Trends and Treatments", Scrip Reports, PJB Publications Ltd, 1996).

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25–30 kg/m$^2$, and obesity as a BMI greater than 30 kg/m$^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (Reductil®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective 5-HT$_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, Psychopharmacol., 1988, 96, 93–100; G. A. Kennett, C. T. Dourish and G. Curzon, Eur. J. Pharmacol., 1987, 141, 429–435) and to accelerate the appearance of the behavioural satiety sequence (S. J. Kitchener and C. T. Dourish, Psychopharmacol., 1994, 113, 369–377). Recent findings from studies with mCPP in normal human volunteers and obese subjects have also shown decreases in food intake. Thus, a single dose of mCPP decreased food intake in female volunteers (A. E. S. Walsh et al., Psychopharmacol., 1994, 116, 120–122) and decreased the appetite and body weight of obese male and female subjects during subchronic treatment for a 14 day period (P. A. Sargeant et al., Psychopharmacol., 1997, 133, 309–312). The anorectic action of mCPP is absent in 5-HT$_{2C}$ receptor knockout mutant mice (L. H. Tecott et al., Nature, 1995, 374, 542–546) and is antagonised by the 5-HT$_{2C}$ receptor antagonist SB-242084 in rats (G. A. Kennett et al., Neuropharmacol., 1997, 36, 609–620). It seems therefore that mCPP decreases food intake via an agonist action at the 5-HT$_{2C}$ receptor.

Other compounds which have been proposed as 5-HT$_{2C}$ receptor agonists for use in the treatment of obesity include the substituted 1-aminoethyl indoles disclosed in EP-A-0655440. CA-2132887 and CA-2153937 disclose that tricyclic 1-aminoethylpyrrole derivatives and tricyclic 1-aminoethyl pyrazole derivatives bind to 5-HT$_{2C}$ receptors and may be used in the treatment of obesity. WO-A-98/30548 discloses aminoalkylindazole compounds as 5-HT$_{2C}$ agonists for the treatment of CNS diseases and appetite regulation disorders. 2-(2,3-Dihydro-1H-pyrrolo[1,2-a]indol-9-yl)ethylamine is disclosed in J.Med.Chem., 1965, 8, 700. The preparation of pyrido[1,2-a]indoles for the treatment of cerebrovascular disorders is disclosed in EP-A-0252643 and EP-A-0167901. The preparation of 10-[(acylamino)ethyl]tetrahydropyrido[1,2a]indoles as anti-ischemic agents is disclosed in EP-A-0279125.

It is an object of this invention to provide selective, directly acting 5HT$_2$ receptor ligands for use in therapy and particularly for use as anti-obesity agents. It is a further object of this invention to provide directly acting ligands selective for 5-HT$_{2B}$ and/or 5-HT$_{2C}$ receptors, for use in therapy and particularly for use as anti-obesity agents. It is a further object of this invention to provide selective, directly acting 5-HT$_{2C}$ receptor ligands, preferably 5-HT$_{2C}$ receptor agonists, for use in therapy and particularly for use as anti-obesity agents.

According to the present invention there is provided a chemical compound of formula (I):

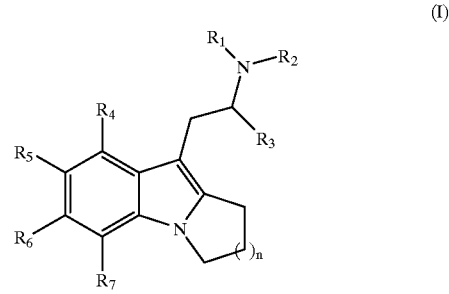

wherein:
n is 1,2 or 3;
R$_1$ and R$_2$ are independently selected from hydrogen and alkyl;
R$_3$ is alkyl;
R$_4$ to R$_7$ are independently selected from hydrogen, halogen, hydroxy, alkyl, aryl, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, or $R_5$ and $R_6$ together form a carbocyclic or heterocyclic ring, and pharmaceutically acceptable salts and prodrugs thereof.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, propyl (n-propyl or isopropyl) or butyl (n-butyl, isobutyl or tertiary-butyl), more preferably methyl.

As used herein, the term "lower alkyl" means methyl, ethyl, propyl (n-propyl or isopropyl) or butyl (n-butyl, isobutyl or tertiary-butyl).

As used herein, the term "aryl" means an aromatic group, such as phenyl or naphthyl, or a heteroaromatic group containing one or more, preferably one, heteroatom, such as pyridyl, pyrrolyl, furanyl and thienyl.

The alkyl and aryl groups may be substituted or unsubstituted. Where substituted, there will generally be 1 to 3 substituents present, preferably 1 substituent. Substituents may include:

carbon-containing groups such as
  alkyl,
  aryl,
  arylalkyl (e.g. substituted and unsubstituted phenyl, substituted
  and unsubstituted benzyl);
halogen atoms and halogen-containing groups such as
  haloalkyl (e.g. trifluoromethyl);
oxygen-containing groups such as
  alcohols (e.g. hydroxy, hydroxyalkyl, aryl(hydroxy)alkyl),
  ethers (e.g. alkoxy, aryloxy, alkoxyalkyl, aryloxyalkyl),
  aldehydes (e.g. carboxaldehyde),
  ketones (e.g. alkylcarbonyl, alkylcarbonylalkyl, arylcarbonyl, arylalkylcarbonyl, arylcarbonylalkyl),
  acids (e.g. carboxy, carboxyalkyl),
  acid derivatives such as esters (e.g. alkoxycarbonyl, alkoxycarbonylalkyl, alkylcarbonyloxy, alkylcarbonyloxyalkyl),
  amides (e.g. aminocarbonyl, mono- or di-alkylaminocarbonyl, aminocarbonylalkyl, mono- or di-alkylaminocarbonylalkyl, arylaminocarbonyl),
  carbamates (e.g. alkoxycarbonylamino, aryloxycarbonylamino, aminocarbonyloxy, mono- or di-alkylaminocarbonyloxy, arylaminocarbonyloxy)
  andureas (e.g. mono- or di-alkylaminocarbonylamino or arylaminocarbonylamino);
nitrogen-containing groups such as
  amines (e.g. amino, mono- or di-alkylamino, aminoalkyl, mono- or di-alkylaminoalkyl),
  azides,
  nitriles (e.g. cyano, cyanoalkyl),
  nitro;
sulfur-containing groups such as
  thiols, thioethers, sulfoxides and sulfones (e.g. alkylthio, alkylsulfinyl, alkylsulfonyl, alkylthioalkyl, alkylsulfinylalkyl, alkylsulfonylallyl, arylthio, arylsulfinyl, arylsulfonyl, arylthioalkyl, arylsulfinylalkyl, arylsulfonylalkyl);
and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O- and "alkoyl" means alkyl-CO-. Alkoxy substituent groups or alkoxy-containing substituent groups may be substituted by one or more alkyl groups.

As used herein, the term "halogen" means a fluorine, chlorine, bromine or iodine radical, preferably a fluorine, chlorine or bromine radical.

As used herein the term "prodrug" means any pharmaceutically acceptable prodrug of the compound of formula (I).

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In a preferred embodiment, the compounds of formula (I) are selected from compounds in which n is 1.

Preferably, the compounds of formula (I) are selected from compounds in which $R_1$ is the same as $R_2$. Preferably, $R_1$ and $R_2$ are both hydrogen. In an embodiment of the invention, $R_1$ is hydrogen and $R_2$ is alkyl (preferably lower alkyl and more preferably methyl) optionally substituted by an aryl (preferably a substituted or unsubstituted phenyl or thienyl group) or by a cycloalkyl group (preferably saturated and preferably selected from a $C_3$, $C_4$, $C_5$, $C_6$ and $C_7$ cycloalkyl group).

Preferably, the compounds of formula (I) are selected from compounds in which $R_3$ is lower alkyl, preferably methyl or ethyl, preferably methyl. The carbon atom to which $R_3$ is bound is an asymmetric carbon atom. It is preferred that this asymmetric carbon atom is in the (S)-configuration, wherein the stereochemical assignment is defined with respect to a compound wherein $R_3$ is an unsubstituted alkyl group.

$R_4$ to $R_7$ are independently selected from hydrogen, halogen, hydroxy, alkyl (including cycloalkyl, halo-alkyl (such as trifluoromethyl) and arylalkyl), aryl, alkoxy (including arylalkoxy), aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, or $R_5$ and $R_6$ together form a carbocyclic or heterocyclic ring.

In an embodiment of the invention, $R_4$ to $R_7$ are independently selected from hydrogen, halogen, hydroxy, alkyl (including cycloalkyl, halo-alkyl (such as trifluoromethyl) and arylalkyl), aryl, alkoxy (including arylalkoxy), aryloxy, alkylthio, alkylsulfoxyl and alkylsulfonyl.

It is preferred that $R_4$ is selected from hydrogen and halogen, preferably hydrogen.

It is preferred that $R_5$ is selected from a substituent group other than hydrogen, and preferably from halogen, alkyl, alkoxy, alkylthio, alkylsulfonyl, monoalkylamino and dialkylamino, and more preferably from halogen (preferably fluoro, chloro and bromo), alkyl (preferably lower alkyl and preferably trifluoromethyl), alkoxy (preferably lower alkoxy) and alkylthio (preferably lower alkylthio).

It is preferred that $R_6$ is selected from halogen (preferably fluoro and chloro) and hydrogen. In an embodiment of the invention, $R_6$ is a substituent group other than hydrogen.

It is preferred that $R_7$ is hydrogen.

In an embodiment of the invention, two or three of $R_4$, $R_5$, $R_6$ and $R_7$, preferably two or three of $R_4$, $R_6$ and $R_7$, and preferably at least $R_4$ and $R_7$, are hydrogen.

In an embodiment of the invention, $R_5$ and $R_6$ may together form a carbocyclic or heterocyclic ring, preferably a heterocyclic ring. The ring may be a 4, 5, 6 or 7-membered ring, preferably a 5- or 6-membered ring, and preferably a 5-membered ring. The ring may be aliphatic or aromatic, preferably aliphatic. Where heterocyclic, the ring may contain 1, 2 or 3 heteroatoms, preferably 1 or 2 heteroatoms. The heteroatoms may be selected from O, S or N. The ring may be substituted or unsubstituted as defined above for "alkyl" groups and "aryl" groups. In a preferred embodiment, $R_5$ and $R_6$ together form a methylenedioxy group which forms a ring with the adjacent carbon atoms of the phenyl group to which it is bound. As used herein, the term "carbocyclic ring" means a ring in which each of the ring atoms are carbon atoms.

In a preferred embodiment, the compounds of formula (I) are selected from 1-(7-chloro-2,3-dihydro-1H-pyrrolo[1,2-a]indol-9-yl)-2-propylamine, 1-(6,7-difluoro-2,3-dihydro-1H-pyrrolo[1,2-a]indol-9-yl)-2-propylamine, 1-(7-bromo-2,3-dihydro-1H-pyrrolo[1,2-a]indol-9-yl)-2-propylamine, 1-(7-methoxy-2,3-dihydro-1H-pyrrolo[1,2-a]indol-9-yl)-2-propylamine and 1-(7-methylthio-2,3-dihydro-1H-pyrrolo[1,2-a]indol-9-yl)-2-propylamine, and particularly the (S)-enantiomers thereof. Where the compounds of formula (I) are in salt form, the fumarate salts are preferred.

The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis.

In a preferred embodiment of the invention, a compound of formula (I) is in the form of its (S)-enantiomer, substantially free of its (R)-enantiomer. As used herein, the term "substantially free of its (R)-enantiomer" means that a composition comprising a compound of formula (I) contains a greater proportion of the (S)-enantiomer of the compound of formula (I) in relation to the (R)-enantiomer of the compound of formula (I). In a preferred embodiment of the present invention, the term "substantially free of its (R)-enantiomer", as used herein, means that the composition contains at least 90% by weight of the (S)-enantiomer and 10% by weight or less of the (R)-enantiomer. In a further preferred embodiment, the term "substantially free of its (R)-enantiomer" means that the composition contains at least 99% by weight of the (S)-enantiomer and 1% or less of the (R)-enantiomer. In another preferred embodiment, the term "substantially free of its (R)-enantiomer" means that the composition contains 100% by weight of the (S)-enantiomer. The above percentages are based on the total amount of a compound of formula (I) present in the composition.

According to a further aspect of the invention, there is provided a compound of formula (I) for use in therapy.

The compounds of formula (I) may be used in the treatment (including prophylactic treatment) of disorders associated with 5-$HT_2$ receptor function. The compounds may act as receptor agonists or antagonists. Preferably, the compounds may be used in the treatment (including prophylactic treatment) of disorders associated with 5-$HT_{2B}$ and/or 5-$HT_{2C}$ receptor function. Preferably, the compounds may be used in the treatment (including prophylactic treatment) of disorders where a 5-$HT_{2C}$ receptor agonist is required.

The compounds of formula (I) may be used in the treatment or prevention of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

According to a further aspect of the invention, there is provided use of a compound of formula (I) in the manufacture of a medicament for the treatment (including prophylaxis) of the above-mentioned disorders. In a preferred embodiment, there is provided use of a compound of formula (I) in the manufacture of a medicament for the treatment (including prophylaxis) of obesity.

According to a further aspect of the invention, there is provided a method of treatment (including prophylaxis) of a disorder selected from the group consisting of the above-mentioned disorders comprising administering to a patient in need of such treatment an effective dose of a compound of formula (I). In a preferred embodiment, there is provided a method of treatment (including prophylaxis) of obesity.

According to a further aspect of the invention, there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

According to a further aspect of the invention, there is provided a method of preparing a compound of formula (I).

Compounds of the invention may be prepared according to Reaction Scheme 1 below. $R_1$ to $R_7$ are as previously defined. The aldehyde (III) may be prepared by reaction of indole (II) with for example, phosphorus oxychloride in dimethylformamide. The chloride (IV) can be formed from the aldehyde (III) by reaction with a suitable bromo-chloro-alkane, iodo-chloro-alkane or chloro-alkane-sulfonate in the presence of a base such as potassium hydroxide in a solvent such as dimethyl sulfoxide. Formation of the iodide (V) may be achieved by reaction of the chloride (IV) with an iodide salt such as sodium iodide in a solvent such as acetonitrile. The aldehyde (VI) may be formed by reaction of the iodide (V) with a trialkyltin hydride in the presence of a reagent such as 1,1'-azobis(cyclohexanecarbonitrile) or azobisisobutyronitrile in a solvent such as toluene. The nitroalkene (VII) may be obtained by reaction of the aldehyde (VI) with a nitroalkane. Compounds of formula (I) can be formed in the reaction of the nitroalkene (VII) with a reducing agent such as lithium aluminium hydride in an ethereal solvent.

Reaction Scheme 1

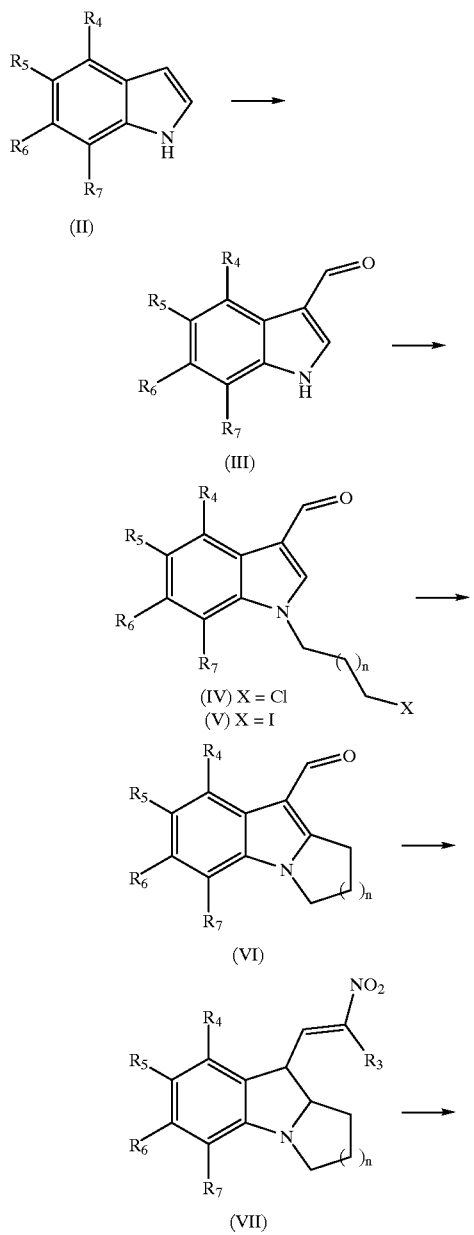

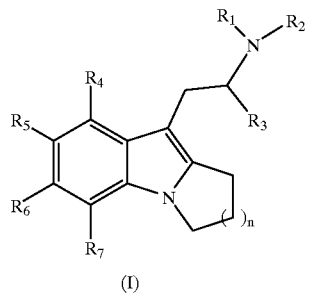

The compounds of formula (I) ($R_1$ and/or $R_2$=alkyl) may be prepared from compounds of formula (I) ($R_1$=$R_2$=H) by standard methods such as reductive alkylation with an appropriate aldehyde or ketone in the presence of a reducing agent such as sodium triacetoxyborohydride, formic acid or sodium cyanoborohydride.

If, in any of the processes mentioned herein, the substituent group $R_4$, $R_5$, $R_6$ or $R_7$ is other than the one required, the substituent group may be converted to the desired substituent by known methods. The substituents $R_4$, $R_5$, $R_6$ or $R_7$ may also need protecting against the conditions under which the reaction is carried out. In such a case, the protecting group may be removed after the reaction has been completed.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

Experimental

Assay Procedures

1. Binding to Serotonin Receptors

The binding of compounds of formula (I) to serotonin receptors was determined in vitro by standard methods. The preparations were investigated in accordance with the assays given hereinafter.

Method (a): For the binding to the $5\text{-}HT_{2C}$ receptor the $5\text{-}HT_{2C}$ receptors were radiolabeled with $[^3H]\text{-}5\text{-}HT$. The affinity of the compounds for $5\text{-}HT_{2C}$ receptors in a CHO cell line was determined according to the procedure of D. Hoyer, G. Engel and H. O. Kalkman, *European J. Pharmacol.*, 1985, 118, 13–23.

Method (b): For the binding to the $5\text{-}HT_{2B}$ receptor the $5\text{-}HT_{2B}$ receptors were radiolabeled with $[^3H]\text{-}5\text{-}HT$. The affinity of the compounds for human $5\text{-}HT_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the $5\text{-}HT_{2A}$ receptor the $5\text{-}HT_{2A}$ receptors were radiolabeled with $[^{125}I]\text{-}DOI$. The affinity of the compounds for $5\text{-}HT_{2A}$ receptors in a CHO cell line was determined according to the procedure of D. J. McKenna and S. J. Peroutka, *J. Neurosci.*, 1989, 9, 3482–90.

The thus determined activity of compounds of formula (I) is shown in Table 1.

TABLE 1

| Compound | $K_i$ (2C) nM | $K_i$ (2B) nM | $K_i$ (2A) nM |
|---|---|---|---|
| Example 1 | 110 | 229 | 457 |
| Example 2 | 97 | 102 | 257 |
| Example 3 | 118 | 220 | 151 |
| Example 5 | 81 | 122 | 448 |
| Example 11 | 84 | 115 | 316 |

2. Functional Activity

The functional activity of compounds of formula (I) was assayed using a Fluorimetric Imaging Plate reader (FLIPR). CHO cells expressing the human $5\text{-}HT_{2C}$ or human $5\text{-}HT_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 $\mu$L/well of assay buffer (Hanks balanced salt solution containing 20 mM Hepes and 2.5 mM probenecid). The drug (dissolved in 50 $\mu$L of the assay buffer) was added at a rate of 70 $\mu$L/sec to each well of the FLIPR 96 well plate during fluorescence measurements. The measurements were taken at 1 sec intervals and the maximum fluorescent signal was measured (approx 10–15 secs after drug addition) and compared with the response produced by 10 $\mu$M 5-HT (defined as 100%) to which it was expressed as a percentage response (relative efficacy). Dose response curves were constructed using Graphpad Prism (Graph Software Inc.).

The thus determined activity of compounds of formula (I) is shown in Table 2.

TABLE 2

| | h5-HT$_{2A}$ | | h5-HT$_{2C}$ | |
|---|---|---|---|---|
| Compound | EC$_{50}$ (nM) | Relative Efficacy (%) | EC$_{50}$ (nM) | Relative Efficacy (%) |
| Example 1 | 3236 | 33 | 96 | 68 |
| Example 2 | >1000 | 12 | 147 | 38 |
| Example 3 | 636 | 22 | 32 | 63 |
| Example 5 | 4020 | 33 | 94 | 69 |
| Example 6 | >10000 | — | 348 | 56 |
| Example 7 | 2620 | 37 | 227 | 59 |
| Example 8 | 921 | 36 | 33 | 58 |
| Example 9 | 792 | 40 | 7 | 81 |
| Example 11 | >10000 | — | 8 | 80 |

3. In Vivo Efficacy

The in vivo efficacy of $5\text{-}HT_{2C}$ agonists was assessed by the ability of the compounds to induce three specific behaviours (5HT$_{2C}$ Syndrome) in rats.

The $5\text{-}HT_{2c}$ syndrome is a rapid screening method to assess the in vivo efficacy of $5\text{-}HT_{2c}$ agonists through their ability to induce three specific behaviours in rats. The animals were dosed with either a positive control (mCPP), test compound or vehicle, either sub-cutaneously or p.o. The animals were observed on an open bench, typically 30, 60 and 180 minutes after dosing and the degree of syndrome was assessed over a two minute period on a scale of 0–3 depending on the presence and severity of splayed limbs, hunched posture and retro-pulsion, the three specific behaviours which constitute the syndrome. Data were analysed using Kruskal-Wallis Analysis of Variance followed with appropriate post-hoc tests. All statistical analysis were conducted using Excel version 7.0 (Microsoft Corp.) and Statistica version 5.0 (Statsoft, Inc.).

The thus determined activity of Example 3 indicates that after a dose of 20 mg/kg s.c. the compound maintains significant pharmacological efficacy for at least 180 minutes.

Synthetic Examples

Example 1

(RS)-1-(7-Chloro-2,3-dihydro-1H-pyrrolo[1,2-a] indol-9-yl)-2-propylamine hydrochloride

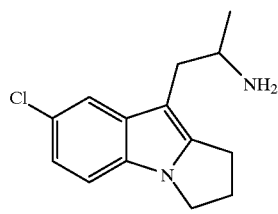

5-Chloroindole-3-carboxaldehyde

To stirred dimethylformamide (20 mL) at 0° C. was added dropwise phosphorus oxychloride (4.6 mL, 49 mmol). The mixture was stirred for 10 min and a solution of 5-chloroindole (5.0 g, 33 mmol) in dimethylformamide (5 mL) was added dropwise. The mixture was heated to 40° C. for 45 min, cooled to room temperature and then treated with a solution of sodium hydroxide (5.9 g, 148 mmol) in water (20 mL). The mixture was heated to 50° C. for 10 min, cooled to room temperature, poured onto crushed ice (100 mL) and filtered. The filter cake was recrystallised (methanol) to give the product as a white solid (3.5 g, 59%): mp 215–216° C.; Found: C, 60.13; H, 3.40; N, 7.75%. $C_9H_6ClNO$ requires: C, 60.19; H, 3.37; N, 7.79%.

5-Chloro-1-(3-chloropropyl)indole-3-carboxaldehyde

To a stirred mixture of powdered potassium hydroxide (85%, 2.6 g, 39 mmol) in methyl sulfoxide (20 mL) was added dropwise a solution of 5-chloroindole-3-carboxaldehyde (3.5 g, 19 mmol) in methyl sulfoxide (5 mL). The mixture was stirred for 30 min and 1-bromo-3-chloropropane (2.9 mL, 29 mmol) was added dropwise. The mixture was stirred for 1 h and partitioned between ethyl acetate (3×40 mL) and water (100 mL). The combined organic extracts were washed (water, brine), dried (sodium sulfate) and concentrated in vacuo. The solid residue was recrystallised (2-propanol) to give the product as a white solid (4.1 g, 82%): mp 107–108° C.; Found: C, 56.51; H, 4.26; N, 5.44%. $C_{12}H_{11}Cl_2NO$ requires: C, 56.27; H, 4.33; N, 5.47%.

5-Chloro-1-(3-iodopropyl)indole-3-carboxaldehyde

A stirred solution of 5-chloro-1-(3-chloropropyl)indole-3-carboxaldehyde (3.8 g, 15 mmol) and sodium iodide (4.5 g, 30 mmol) in acetonitrile (50 mL) under argon was heated under reflux for 18 h, cooled to room temperature and partitioned between ether (3×30 mL) and water (50 mL). The combined organic extracts were washed (aqueous sodium metabisulfite solution, water, brine), dried (sodium sulfate) and concentrated in vacuo to give the product as a yellow oil (5.0 g, 96%) which was used immediately.

7-Chloro-2,3-dihydro-1H-pyrrolo[1,2-a]indole-9-carboxaldehyde

To a stirred solution of 5-chloro-1-(3-iodopropyl)indole-3-carboxaldehyde (5.0 g, 14 mmol) in toluene (75 mL) at reflux under argon was added dropwise over 2 h a solution of 1,1'-azobis(cyclohexanecarbonitrile) (3.5 g, 14 mmol) and tri-n-butyltin hydride (7.8 mL, 29 mmol) in toluene (75 mL). The mixture was stirred for 3 h, cooled to room temperature, and potassium fluoride (3.5 g, 60 mmol) and water (15 mL) were added. The mixture was stirred for 18 h and filtered through a pad of kieselguhr. The filter-cake was washed (ethyl acetate) and the filtrate was concentrated in vacuo, purified by column chromatography [$SiO_2$; ethyl acetate-hexane (9:1)] and recrystallised (methanol) to give the product as a white solid (1.1 g, 36%): mp 179–180° C.; Found: C, 65.54; H, 4.61; N, 6.38%. $C_{12}H_{10}ClNO$ requires: C, 65.61; H, 4.59; N, 6.37%.

1-(7-Chloro-2,3-dihydro-1H-pyrrolo[1,2-a]indol-9-yl)-2-nitro-1-propene

A stirred solution of 7-chloro-2,3-dihydro-1H-pyrrolo[1,2-a]indole-9-carboxaldehyde (1.0 g, 4.6 mmol) and ammonium acetate (0.4 g, 5.2 mmol) in nitroethane (10 mL) was heated to 100° C. for 1 h, cooled to room temperature, diluted with methanol (30 mL), cooled to 0° C., and filtered. The filter-cake was recrystallised (toluene) to give the product as yellow needles (0.58 g, 46%): mp 162–1623° C.; Found: C, 60.68; H, 4.67; N, 9.98%. $C_{14}H_{13}ClN_2O_2$ requires: C, 60.77; H, 4.73; N, 10.12%.

(RS)-1-(7-Chloro-2,3-dihydro-1H-pyrrolo[1,2-a]indol-9-yl)-2-propylamine hydrochloride To a stirred solution of lithium aluminium hydride (1.0 M in THF, 2.7 mL, 2.7 mmol) in added THF (5 mL) under argon was added dropwise a solution of 1-(7-chloro-2,3-dihydro-1H-pyrrolo[1,2-a]indol-9-yl)-2-nitro-1-propene (0.5 g, 1.8 mmol) in THF (10 mL). The mixture was heated under reflux for 4 h and cooled to 0° C. To the mixture was added dropwise aqueous potassium sodium tartrate solution (50 mL) and the mixture was stirred for 30 min and filtered through kieselguhr. The filtrate was extracted with dichloromethane (3×30 mL). The combined organic extracts were washed (water, brine), dried (sodium sulfate), concentrated in vacuo, treated with ethereal hydrogen chloride (1.0 M, 2 mL, 2 mmol) and concentrated in vacuo. The concentrate was recrystallised (2-propanol) to give the title compound as a white solid (0.23 g, 45%): mp 272–273° C.; Found: C, 57.86; H, 6.37; N, 9.41%. $C_{14}H_{17}ClN_2 \cdot HCl \cdot 0.25H_2O$ requires: C, 58.03; H, 6.39; N, 9.67%.

Example 2

(RS)-1-(6,7-Difluoro-2,3-dihydro-1H-pyrrolo[1,2-a] indol-9-yl)-2-propylamine hydrochloride

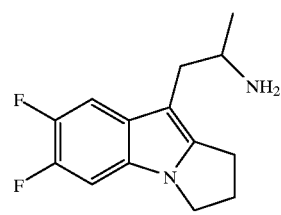

5,6-Difluoroindole-3-carboxaldehyde 5,6-Difluoroindole-3-carboxaldehyde was prepared from 5,6-difluoroindole according to the method described in Example 1 to give 2.9 g (78%) of the product as a pale yellow solid: mp 236–238° C.; Found: C, 58.34; H, 2.79; N, 7.27%. $C_9H_5F_2NO \cdot 0.25H_2O$ requires: C, 58.23; H, 2.99; N, 7.55%.

5,6-Difluoro-1-(3-chloropropyl)indole-3-carboxaldehyde 5,6-Difluoro-1-(3-chloropropyl)indole-3-carboxaldehyde was prepared from 5,6-difluoroindole-3-carboxaldehyde according to the method described in Example 1 to give the 2.9 g (78%) of the product as a yellow solid: mp 111–113° C.; Found: C, 55.87; H, 3.94; N, 5.40%. $C_{12}H_{10}ClF_2NO$ requires: C, 55.94; H, 3.91; N, 5.44%.

5,6-Difluoro-1-(3-iodopropyl)indole-3-carboxaldehyde 5,6-Difluoro-1-(3-iodopropyl)indole-3-carboxaldehyde was prepared from 5,6-difluoro -1-(3-chloropropyl)indole-3-carboxaldehyde according to the method described in Example 1 with the following modification: the crude product was purified by column chromatography [$SiO_2$; hexane-ethyl acetate (3:2)] to give the product as a yellow solid (2.7 g, 87%). A sample recrystallised from ethyl acetate-hexane gave mp 95–97° C.; Found: C, 41.42; H, 2.94; N, 3.99%. $C_{12}H_{10}F_2INO$ requires: C, 41.28; H, 2.89; N, 4.01%.

6,7-Difluoro-2,3-dihydro-1H-pyrrolo[1,2-a]indole-9-carboxaldehyde 6,7-Difluoro-2,3-dihydro-1H-pyrrolo[1,2-a]indole-9-carboxaldehyde was prepared from 5,6-difluoro-1-(3-iodopropyl)indole-3-carboxaldehyde according to the method described in Example 1 with the following modification: the crude product was purified by column chromatography [$SiO_2$; hexane-ethyl acetate (1:1)] to give the product as a pale yellow solid (1.1 g, 66%) which was used immediately without further purification.

1-(6,7-Difluoro-2,3-dihydro-1H-pyrrolo[1,2-a]indol-9-yl)-2-nitro-1-propene 1-(6,7-Difluoro-2,3-dihydro-1H-pyrrolo[1,2-a]indol-9-yl)-2-nitro-1-propene was prepared from 6,7-difluoro-2,3-dihydro-1H-pyrrolo[1,2-a]indole-9-carboxaldehyde according to the method described in Example 1 with the following modifications: the reaction mixture was stirred at 100° C. for 1 h, cooled to room temperature and partitioned between ethyl acetate (3×30 mL) and water. The combined organic extracts were washed (brine), dried (magnesium sulfate) and concentrated in vacuo to give the crude product which was purified by column chromatography [$SiO_2$; hexane-ethyl acetate (3:1)] to give the product as a yellow solid (0.9 g, 72%). A sample recrystallised from methanol gave mp 156–8° C.; Found: C, 62.63; H, 5.42; N, 9.30%. $C_{14}H_{12}F_2N_2O_2.0.3C_6H_{14}$ requires: C, 62.40; H, 5.37; N, 9.21%.

(RS)-1-(6,7-Difluoro-2,3-dihydro-1H-pyrrolo[1,2-a]indol-9-yl)-2-propylamine hydrochloride (RS)-1-(6,7-Difluoro-2,3-dihydro-1H-pyrrolo[1,2-a]indol-9-yl)-2-propylamine hydrochloride was prepared from 1-(6,7-difluoro-2,3-dihydro-1H-pyrrolo[1,2-a]indol-9-yl)-2-nitro-1-propene according to the method described in Example 1 with the following modifications: the reaction mixture was heated under reflux for 4 h, cooled to 0° C. and poured into aqueous potassium sodium tartrate solution (150 mL) and diethyl ether (100 mL). The mixture was stirred for 30 min, filtered through celite® and the filtrate was extracted with ethyl acetate (2×50 mL). The combined organic extracts were washed (brine), dried (magnesium sulfate), concentrated in vacuo, treated with ethereal hydrogen chloride (1.0 M, 2 mL, 2 mmol) and concentrated in vacuo. The residue was recrystallised (ethyl acetate, 2-propanol) to give the title compound as a white solid (0.55 g, 63%): mp 264–266° C. Found: C, 58.67; H, 6.09; N, 9.65%. $C_{14}H_{16}F_2N_2.HCl$ requires: C, 58.64; H, 5.98; N, 9.76%.

Example 3

(RS)-1-(7-Methoxy-2,3-dihydro-1H-pyrrolo[1,2-a]indol-9-yl)-2-propylamine fumarate

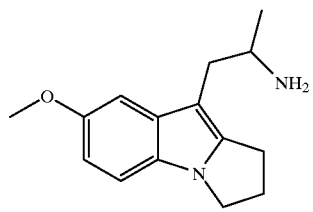

5-Methoxyindole-3-carboxaldehyde

5-Methoxyindole-3-carboxaldehyde was prepared from 5-methoxyindole according to the method described in Example 1 to give 5.1 g (85%) of the product as a white solid: mp 179–180° C.; Found: C, 68.37; H, 5.15; N, 7.98%. $C_{10}H_9NO_2$ requires C, 68.56; H, 5.18; N, 7.99%.

1-(3-Chloropropyl)-5-methoxy-indole-3-carboxaldehyde 1-(3-Chloropropyl)-5-methoxy-3-carboxaldehyde was prepared from 5-methoxyindole-3-carboxaldehyde according to the method described in Example 1 with the following modifications: the reaction mixture was stirred for 18 h, poured into ice-water (100 mL) and filtered. The filter-cake was recrystallised [isopropyl ether, 2-propanol (1:1)] to give the product as a white, crystalline solid (4.6 g, 63%): mp 75–76° C.; NMR $\delta_H$ (400 MHz, $CDCl_3$) 2.29 (2H, quintet, J 6 Hz) 3.46 (2H, t, J 6 Hz) 3.87 (3H, s) 4.36 (2H, t, J 6 Hz) 6.95(1H, dd, J 2.5, 9 Hz) 7.27 (1H, d, J 9 Hz) 7.69(1H, s) 7.77(1H, d, J 2.5 Hz) 9.94 (1H, s).

1-(3-Iodopropyl)-5-methoxy-indole-3-carboxaldehyde 1-(3-Iodopropyl)-5-methoxy-indole-3-carboxaldehyde was prepared from 1-(3-chloropropyl)-5-methoxy-indole-3-carboxaldehyde according to the method described in Example 1 with the following modification: the reaction mixture was heated under reflux for 18 h, cooled to room temperature and partitioned between ether (3×30 mL) and water (50 mL). The combined organic extracts were washed (aqueous sodium metabisulfite solution, water, brine), dried (sodium sulfate) and concentrated in vacuo. The crude product was purified by column chromatography [$SiO_2$; heptane-ethyl acetate (3:1)] to give the product as a yellow oil (4.9 g, 78%) which was used immediately.

7-Methoxy-2,3-dihydro-1H-pyrrolo[1,2-a]indole-9-carboxaldehyde

7-Methoxy-2,3-dihydro-1H-pyrrolo[1,2-a]indole-9-carboxaldehyde was prepared from 1-(3-iodopropyl)-5-methoxy-indole-3-carboxaldehyde according to the method described in Example 1 to give 0.41 g (13%) of the product as a white solid: mp 151–152° C.; Found: C, 72.25; H, 6.10; N, 6.46%. $C_{13}H_{13}NO_2$ requires: C, 72.54; H, 6.09; N, 6.50%.

1-(7-Methoxy-2,3-dihydro-1H-pyrrolo[1,2-a]indol-9-yl)-2-nitro-1-propene 1-(7-Methoxy-2,3-dihydro-1H-pyrrolo[1,2-a]indol-9-yl)-2-nitro-1-propene was prepared from 7-methoxy-2,3-dihydro-1H-pyrrolo[1,2-a]indole-9-carboxaldehyde according to the method described in Example 1 with the following modification: the reaction mixture was heated to 100° C. for 1 h, cooled to room temperature and partitioned between ethyl acetate (2×20 mL) and water (30 mL). The combined organic extracts were washed (water, brine), dried (sodium sulfate), concentrated in vacuo and purified by column chromatography [SiO$_2$; ethyl acetate-heptane (1:1)] to give the product as yellow needles (0.46 g, 91%): mp 143° C.; Found: C, 66.32; H, 5.89; N, 10.27%. C$_{15}$H$_{16}$N$_2$O$_3$ requires: C, 66.16; H, 5.92; N, 10.28%.

(RS)-1-(7-Methoxy-2,3-dihydro-1H-pyrrolo[1,2-a]indol-9-yl)-2-propylamine fumarate (RS)-1-(7-Methoxy-2,3-dihydro-1H-pyrrolo[1,2-a]indol-9-yl)-2-propylamine fumarate was prepared from 1-(7-methoxy-2,3-dihydro-1H-pyrrolo[1,2-a]indol-9-yl)-2-nitro-1-propene according to hthe method described in Example 1 with the following modifications: the reaction mixture was heated under reflux for 4 h, cooled to 0° C. and aqueous potassium sodium tartrate solution (50 mL) was added slowly. The mixture was stirred for 30 min, filtered through a pad of kieselguhr and the filtrate was extracted with dichloromethane (3×30 mL). The combined organic extracts were washed (water, brine), dried (sodium sulfate) and concentrated in vacuo. The concentrate was dissolved in 2-propanol (1 mL) and added to a solution of fumaric acid (0.17 g, 1.5 mmol) in 2-propanol (20 mL) at 50° C. The solution was cooled to 0° C. and filtered. The filter-cake was washed (2-propanol, ether) and dried to give the title compound as a white solid (0.22 g, 42%): mp 194–196° C.; Found: C, 63.27; H, 6.80; N, 7.69%. C$_{19}$H$_{24}$N$_2$O$_5$ requires: C, 63.32; H, 6.71; N, 7.77%.

Example 4

(RS)-1-(8-Chloro-2,3-dihydro-1H-pyrrolo[1,2-a]indol-9-yl)-2-propylamine hemifumarate

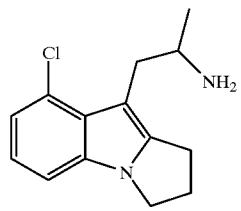

4-Chloroindole-3-carboxaldehyde

4-Chloroindole-3-carboxaldehyde was prepared from 4-chloroindole according to the method described in Example 1 to give 7.8 g (100%) of the product which was used without further purification.

4-Chloro-1-(3-chloropropyl)indole-3-carboxaldehyde

4-Chloro-1-(3-chloropropyl)indole-3-carboxaldehyde was prepared from 4-chloroindole-3-carboxaldehyde according to the method described in Example 1 to give 3.8 g (45%, from 4-chloroindole) of the product as a white solid: mp 89° C.; Found: C, 56.16; H, 4.23; N, 5.40%. C$_{12}$H$_{11}$Cl$_2$NO requires: C, 56.27; H, 4.33; N, 5.47%.

4-Chloro-1-(3-iodopropyl)indole-3-carboxaldehyde

4-Chloro-1-(3-iodopropyl)indole-3-carboxaldehyde was prepared from 4-chloro-1-(3-chloropropyl)indole-3-carboxaldehyde according to the method described in Example 1 to give 4.2 g (83%) of the product as a yellow solid which was used immediately without further purification.

8-Chloro-2,3-dihydro-1H-pyrrolo[1,2-a]indole-9-carboxaldehyde

8-Chloro-2,3-dihydro-1H-pyrrolo[1,2-a]indole-9-carboxaldehyde was prepared from 4-chloro-1-(3-iodopropyl)indole-3-carboxaldehyde according to the method described in Example 1 to give 1.0 g (39%) of the product as a white solid; mp 160–161° C.; Found: C, 65.70; H, 4.54; N, 6.34%. C$_{12}$H$_{10}$NClO requires: C, 65.61; H, 4.59; N, 6.37%.

1-(8-Chloro-2,3-dihydro-1H-pyrrolo[1,2-a]indol-9-yl)-2-nitro-1-propene 1-(8-Chloro-2,3-dihydro-1H-pyrrolo[1,2-a]indol-9-yl)-2-nitro-1-propene was prepared from 8-chloro-2,3-dihydro-1H-pyrrolo[1,2-a]indole-9-carboxaldehyde according to the method described in Example 3 to give 1.1 g (95%) of the product as yellow needles: mp 137–138° C.; Found: C, 60.68; H, 4.73; N, 9.95%. C$_{14}$H$_{13}$N$_2$ClO$_2$ requires: C, 60.77; H, 4.73; N, 10.12%.

(RS)-1-(8-Chloro-2,3-dihydro-1H-pyrrolo[1,2-a]indol-9-yl)-2-propylamine hemifumarate (RS)-1-(8-Chloro-2,3-dihydro-1H-pyrrolo[1,2-a]indol-9-yl)-2-propylamine hemifumarate was prepared from 1-(8-chloro-2,3-dihydro-1H-pyrrolo[1,2-a]indol-9-yl)-2-nitro-1-propene according to the method described in Example 3 to give 0.71 g (53%) of the product as a white solid. A sample recrystallised from 2-propanol gave mp 207–208° C.; Found: C, 61.67; H, 6.31; N, 8.79%. C$_{14}$H$_{17}$N$_2$Cl.0.5C$_4$O$_4$.0.25H$_2$O requires: C, 61.73; H, 6.31; N, 9.00%.

Example 5

(RS)-1-(7-Bromo-2,3-dihydro-1H-pyrrolo[1,2-a]indol-9-yl)-2-propylamine fumarate

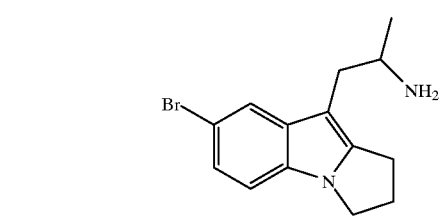

5-Bromoindole-3-carboxaldehyde

5-Bromoindole-3-carboxaldehyde was prepared from 5-bromoindole according to the method described in Example 1 to give 5.1 g (89%) of the product as a beige solid which was used without further purification: IR ν$_{max}$ (Nujol)/cm$^{-1}$ 3222, 2925, 2855, 1712, 1644, 1524, 1459, 1441, 1378, 1290, 1129, 1096, 856, 799, 782, 728, 673, 609 and 573; NMR δ$_H$ (400 MHz, CDCl$_3$) 6.31 (1H, dd, J 2, 8.5 Hz) 6.41 (1H, d, J 8.5 Hz) 7.13 (1H, d, J 2 Hz) 7.26 (1H, s) 8.84 (1H, s) 11.21 (1H, s).

5-Bromo-1-(3-chloropropyl)indole-3-carboxaldehyde

5-Bromo-1-(3-chloropropyl)indole-3-carboxaldehyde was prepared from 5-bromoindole-3-carboxaldehyde according to the method described in Example 1 with the following modification: the reaction mixture was stirred for 18 h, poured into ice-water (200 mL) and filtered. The filter-cake was washed (water, heptane), dried and purified by column chromatography (SiO$_2$; ethyl acetate) to give 4.6 g (77%) of the product as a white solid: IR ν$_{max}$ (Nujol)/cm$^{-1}$ 2925, 2855, 1660, 1610, 1532, 1469, 1402, 1378, 1302, 1171, 1195, 1035, 968, 818, 786, 722, 666, 622 and 610; NMR δ$_H$ (400 MHz, CDCl$_3$) 2.32 (2H, m) 3.48 (2H, t, J 6.5 Hz) 4.41 (2H, t, J 6.5 Hz) 7.28 (1H, d, J 9 Hz) 7.44 (1H, dd, J 2, 8.5 Hz) 7.76 (1H, s) 8.47 (1H, d, J 3 Hz) 9.98 (1H, s).

5-Bromo-1-(3-iodopropyl)indole-3-carboxaldehyde

5-Bromo-1-(3-iodopropyl)indole-3-carboxaldehyde was prepared from 5-chloro-1-(3-chloropropyl)indole-3-carboxaldehyde according to the method described in Example 1 to give 6.0 g (100%) of the product as a yellow oil which was immediately.

7-Bromo-2,3-dihydro-1H-pyrrolo[1,2-a]indole-9-carboxaldehyde

7-Bromo-2,3-dihydro-1H-pyrrolo[1,2-a]indole-9-carboxaldehyde was prepared from 5-bromo-1-(3-iodopropyl)indole-3-carboxaldehyde according to the method described in Example 1 to give 1.2 g (32%) of the product as a white solid: mp 189–191° C.; IR ν$_{max}$ (Nujol)/cm$^{-1}$ 2925, 2855, 1651, 1606, 1534, 1452, 1442, 1397, 1377, 1360, 1314, 1288, 1245, 1050, 1038, 802, 775, and 571; NMR δ$_H$ (400 MHz, CDCl$_3$) 2.72 (2H, m) 3.25 (2H, t, J 7.5 Hz) 4.08 (2H, t, J 7 Hz) 7.07 (1H, d, J 8.5 Hz) 7.29 (1H, d, J 8.5 Hz) 8.31 (1H, s) 9.90 (1H, s).

1-(7-Bromo-2,3-dihydro-1H-pyrrolo[1,2-a]indol-9-yl)-2-nitro-1-propene 1-(7-Bromo-2,3-dihydro-1H-pyrrolo[1,2-a]indol-9-yl)-2-nitro-1-propene was prepared from 7-bromo-2,3-dihydro-1H-pyrrolo[1,2-a]indole-9-carboxaldehyde according to the method described in Example 1 to give 1.1 g (81%) of the product as yellow needles: mp 173° C.; Found: C, 52.44; H, 4.10; N, 8.75%. C$_{14}$H$_{13}$N$_2$BrO requires: C, 52.36; H, 4.08; N, 8.72%.

(RS)-1-(7-Bromo-2,3-dihydro-1H-pyrrolo[1,2-a]indol-9-yl)-2-propylamine fumarate (RS)-1-(7-Bromo-2,3-dihydro-1H-pyrrolo[1,2-a]indol-9-yl)-2-propylamine fumarate was prepared from 1-(7-bromo-2,3-dihydro-1H-pyrrolo[1,2-a]indol-9-yl)-2-nitro-1-propene according to the method described in Example 3 to give 0.38 g (60%) of the product as a white solid: mp 181–183° C.; IR ν$_{max}$ (Nujol)/cm$^{-1}$ 2925, 2855, 1702, 1632, 1580, 1524, 1464, 1378, 1317, 1277, 1222, 1167, 1100, 1049, 986, 897, 783 722, 652 and 564; NMR δ$_H$ (400 MHz, DMSO-d$_6$) 1.14 (3H, d, J 7 Hz) 2.56 (2H, m) 2.96 (3H, m) 3.79 (1H, m) 4.05 (2H, t, J 7 Hz) 6.46 (2H, s) 7.15 (1H, dd, J 2, 8.5 Hz) 7.27 (1H, d, J 8.5 Hz) 7.72 (1H, d, J 2 Hz).

Example 6

(RS)-1-(7-Methyl-2,3-dihydro-1H-pyrrolo[1,2-a]indol-9-yl)-2-propylamine fumarate

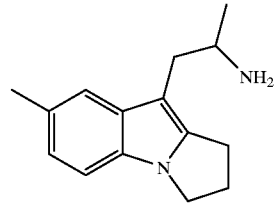

5-Methylindole-3-carboxaldehyde

5-Methylindole-3-carboxaldehyde was prepared from 5-methylindole according to the method described in Example 1 to give 2.06 (42%) of the product as a pink solid: mp 148–149° C.; IR ν$_{max}$ (Nujol)/cm-1 3145, 2924, 1639, 1523, 1450, 1133, 805 and 616; NMR δ$_H$ (400 MHz, DMSO-d$_6$) 2.41 (3H, s), 3.32 (3H, s), 7.08 (1H, d, J 6.7 Hz), 7.39 (1H, d, J 8.2 Hz), 7.90 (1H, s), 8.22 (1H, s), 9.90 (1H, s) and 12.01 (1H, br. s); Found: C, 75.24; H, 5.67; N, 8.83%. C$_{10}$H$_9$NO requires: C, 75.45; H, 5.70; N, 8.97%.

1-(3-Chloropropyl)-5-methyl-indole-3-carboxaldehyde 1-(3-Chloropropyl)-5-methyl-indole-3-carboxaldehyde was prepared from 5-methylindole-3-carboxaldehyde according to the method described in Example 1 to give 2.26 g (76%) of the product as an off-white solid: mp 89–90° C.; IR ν$_{max}$ (Nujol)/cm$^{-1}$ 2956, 1659, 1536, 1403, 1171, 820 and 786; NMR δ$_H$ (400 MHz, CDCl$_3$) 2.27–2.34 (2H, m), 2.47 (3H, s), 3.46 (2H, t, J 6.2 Hz), 4.38 (2H, t, J 6.6 Hz), 7.16 (1H, d, J 10 Hz), 7.28 (1H, d, J 8.4 Hz), 7.70 (1H, s), 8.12 (1H, s) and 9.97 (1H, s); Found: C, 66.12; H, 6.00; N, 5.88%. C$_{13}$H$_{14}$ClNO requires: C, 66.24; H, 5.99; N, 5.94%.

1-(3-Iodopropyl)-5-methyl-indole-3-carboxaldehyde 1-(3-Iodopropyl)-5-methyl-indole-3-carboxaldehyde was prepared from 1-(3-chloropropyl)-5-methyl-indole-3-carboxaldehyde according to the method described in Example 1 to give the product as pink oil which was used immediately without further purification.

7-Methyl-2,3-dihydro-1H-pyrrolo[1,2-a]indole-9-carboxaldehyde

7-Methyl-2,3-dihydro-1H-pyrrolo[1,2-a]indole-9-carboxaldehyde was prepared from 1-(3-iodopropyl)-5-methyl-indole-3-carboxaldehyde according to the method described in Example 1 to give 0.74 g (40%) of the product as a white solid: mp 148–149° C.; IR ν$_{max}$ (Nujol)/cm$^{-1}$ 2953, 1643, 1448, 1357, 1033 and 814; NMR δ$_H$ (400 MHz, CDCl$_3$) 2.45 (3H, s), 2.68–2.73 (2H, m), 3.27 (2H, t, J 7.7 Hz), 4.09 (2H, t, J 7.5 Hz), 7.04 (1H, d, J 8.5 Hz), 7.13 (1H, d, J 8.6 Hz), 8.00 (1H, s) and 9.96 (1H, s)

1-(7-Methyl-2,3-dihydro-1H-pyrrolo[1,2-a]indol-9-yl)-2-nitro-1-propene 1-(7-Methyl-2,3-dihydro-1H-pyrrolo[1,2-a]indol-9-yl)-2-nitro-1-propene was prepared from 7-methyl-2,3-dihydro-1H-pyrrolo[1,2-a]indole-9-carboxaldehyde according to the method described in Example 1 to give 0.73 g (68%) of the product as an orange solid: mp 138–139° C.; IR $\nu_{max}$ (Nujol)/cm$^{-1}$ 2925, 1634, 1458, 1266, 1042, 977 and 799; NMR $\delta_H$ (400 MHz, CDCl$_3$) 2.42 (3H, s), 2.46 (3H, s), 2.65–2.70 (2H, s), 3.10 (2H, t, J 7.0 Hz), 4.13 (2H, t, J 7.0 Hz), 7.04 (1H, d, J 7.0 Hz), 7.15 (1H, d, J 8.0 Hz), 7.41 (1H, s) and 8.39 (1H, s); Found: C, 70.57; H, 6.76; N, 11.14%. C$_{15}$H$_{16}$N$_2$O$_2$ requires: C, 70.29; H, 6.29; N, 10.92%.

(RS)-1-(7-Methyl-2,3-dihydro-1H-pyrrolo[1,2-a]indol-9-yl)-2-propylamine fumarate (RS)-1-(7-Methyl-2,3-dihydro-1H-pyrrolo[1,2-a]indol-9-yl)-2-propylamine fumarate was prepared from 1-(7-methyl-2,3-dihydro-1H-pyrrolo[1,2-a]indol-9-yl)-2-nitro-1-propene according to the method described in Example 3 to give 0.61 g (71%) of the title compound as an off-white solid: mp darkens at 140° C., melts 156–157° C.; IR $\nu_{max}$ (Nujol)/cm$^{-1}$ 2922, 1697, 1461, 1378, 979, 791 and 652; NMR $\delta_H$ (400 MHz, DMSO-d$_6$) 1.25 (3H, d, J 6.5 Hz), 2.47 (3H, s), 2.63–2.67 (1H, m), 2.80–2.85 (1H, m), 2,94–3.08 (3H, m), 3.43–3.53 (2H, m), 4.10 (2H, t, J 7.4 Hz), 6.52 (2H, s), 6.97 (1H, d, J 8.1 Hz), 7.26 (1H, d, J 7.9 Hz) and 7.36 (1H, s); Found: C, 64.71; H, 7.30; N, 8.12%. C$_{15}$H$_{20}$N$_2$.C$_4$H$_4$O$_4$.0.5H$_2$O requires: C, 64.57; H, 7.13; N, 7.93%.

Example 7

(RS)-1-[6,7-(Methylenedioxy)-2,3-dihydro-1H-pyrrolo[1,2-a]indol-9-yl]-2-propylamine fumarate

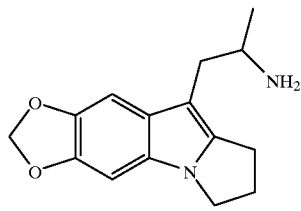

5,6-(Methylenedioxy)indole-3-carboxaldehyde 5,6-(Methylenedioxy)indole-3-carboxaldehyde was prepared from 5,6-(methylenedioxy)indole according to the method described in Example 1 to give 1.9 g (85%) of the product as a yellow solid: mp darkens and decomposes over 180–190° C.; IR $\nu_{max}$ (nujol)/cm$^{-1}$ 3233, 2925, 1630, 1472, 1294, 1177 and 937; NMR $\delta_H$ (400 MHz, DMSO-d$_6$) 6.01 (2H, s), 7.03 (1H, s), 7.46 (1H, s), 8.08 (1H, s), 9.83 (1H, s) and 12.90 (1H, br. s).

1-(3-Chloropropyl)-5,6-(methylenedioxy)-indole-3-carboxaldehyde 1-(3-Chloropropyl)-5,6-(methylenedioxy)-indole-3-carboxaldehyde was prepared from 5,6-(methylenedioxy)indole-3-carboxyaldehyde according to the method described in Example 1 to give 2.06 g (79%) of the product as light-brown crystals: mp 108–109° C.; IR $\nu_{max}$ (nujol)/cm$^{-1}$ 2924, 1656, 1534, 1250, 1163 and 939; NMR $\delta_H$ (400 MHz, CDCl$_3$) 2.27–2.30 (2H, m), 3.47 (2H, t, J 6 Hz), 4.30 (2H, t, J 6 Hz), 5.98 (2H, s), 6.82 (1H, s), 7.59 (1H, s), 7.70 (1H, s) and 9.90 (1H, s); Found: C, 58.92; H, 4.60; N, 5.23%. C$_{13}$H$_{12}$ClNO$_3$ requires: C, 58.77; H, 4.55; N, 5.27%.

1-(3-Iodopropyl)-5,6-(methylenedioxy)-indole-3-carboxaldehyde 1-(3-Iodopropyl)-5,6-(methylenedioxy)-indole-3-carboxaldehyde was prepared from 1-(3-chloropropyl)-5,6-(methylenedioxy)-indole-3-carboxaldehyde according to the method described in Example 1 to give the product as a brown solid which was used immediately without further purification.

6,7-(Methylenedioxy)-2,3-dihydro-1H-pyrrolo[1,2-a]indole-9-carboxaldehyde

This was prepared from 1-(3-iodopropyl)-5,6-(methylenedioxy)-indole-3-carboxaldehyde according to the method described in Example 1 to give 1.0 g (75%) of the product as an off-white solid: mp 169–170° C.; IR $\nu_{max}$ (Nujol)/cm$^{-1}$ 2924, 1639, 1645, 1244, 1133 and 944; NMR $\delta_H$ (400 MHz, CDCl$_3$) 2.68 (2H, quint, J 7.2 Hz), 7.20 (2H, t, J 7.2 Hz), 4.05 (2H, t, J 7.1 Hz), 5.95 (2H, s), 6.70 (1H, s), 7.63 (1H, s) and 9.89 (1H, s).

1-[6,7-(Methylenedioxy)-2,3-dihydro-1H-pyrrolo[1,2-a]indol-9-yl)-2-nitro-1-propene 1-[6,7-(Methylenedioxy)-2,3-dihydro-1H-pyrrolo[1,2-a]indol-9-yl)-2-nitro-1-propene was prepared from 5,6-(methylenedioxy)-2,3-dihydro-1H-pyrrolo[1,2-a]indole-9-carboxaldehyde according to the method described in Example 1 to give 0.76 g (62%) of the product as an orange solid: mp darkens over 202–210° C.; IR $\nu_{max}$ (Nujol)/cm$^{-1}$ 2924, 1635, 1458, 1246, 1197 and 861; NMR $\delta_H$ (400 MHz, CDCl$_3$) 2.40 (3H, s), 2.65 (2H, quint, J 7.4 Hz), 3.06 (2H, t, J 7.6 Hz), 4.07 (2H, t, J 7.1 Hz), 5.95 (2H, s) 6.71 (1H, s), 7.00 (1H, s) and 8.30 (1H, s); Found: C, 62.31; H, 5.25; N, 9.93%. C$_{15}$H$_{14}$N$_2$O$_4$ requires: C, 62.93; H, 4.93; N, 9.78%.

(RS)-1-[(6,7-Methylenedioxy)-2,3-dihydro-1H-pyrrolo[1,2-a]indol-9-yl)-2-propylamine fumarate (RS)-1-[(6,7-Methylenedioxy)-2,3-dihydro-1H-pyrrolo[1,2-a]indol-9-yl)-2-propylamine fumarate was prepared from 1-[6,7-(methylenedioxy)-2,3-dihydro-1H-pyrrolo[1,2-a]indol-9-yl)-2-nitro-1-propene according to the method described in Example 3 to give 0.13 g (14%) of the title compound as an off-white solid: mp darkens over 135–140° C.; IR $\nu_{max}$ (Nujol)/cm$^{-1}$ 2923, 1632, 1466, 1235, 1039 and 652; NMR $\delta_H$ (400 MHz, DMSO-d$_6$) 1.12 (3H, d, J 6.6 Hz), 2.46–2.53 (1H, m), 2.63–2.69 (1H, dd, J, 14.1, 8.4 Hz), 2.81–2.93 (3H, m), 3.26–3.39 (2H, m), 3.94 (2H, t, J 7.0 Hz), 5.89 (2H, s), 6.40 (2H, s), 6.89 (1H, s) and 7.01 (1H, s); Found: C, 58.48; H, 5.79; N, 7.25%. C$_{15}$H$_{18}$N$_2$O$_2$C$_4$H$_4$O$_4$.H$_2$O requires: C, 58.16; H, 6.16; N, 7.14%.

Examples 8 and 9

Enantiomer 1 and Enantiomer 2 of 1-(7-Methoxy-2,3-dihydro-1H-pyrrolo[1,2-a]indol-9-yl)-2-propylamine fumarate

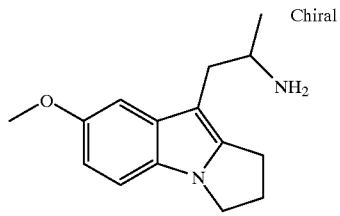

(RS)-1-(7-Methoxy-2,3-dihydro-1H-pyrrolo[1,2-a]indol-9-yl)-2-(trifluoroacetamido)-propane To a stirred solution of (RS)-1-(7-methoxy-2,3-dihydro-1H-pyrrolo[1,2-a]indol-9-yl)-2-propylamine (0.28 g, 1.1 mmol) in dichloromethane (10 mL) at 0° C. was added dropwise trifluoroacetic anhydride (0.18 mL, 1.3 mmol). The mixture was stirred for 1 h, concentrated in vacuo and purified by column chromatography (SiO$_2$; ether) to afford the product (0.39 g, 100%) as a beige solid: mp 131–3° C.; IR v$_{max}$ (Nujol)/cm$^{-1}$ 3307, 3105, 2925, 2855, 2727, 1784, 1695, 1501, 1377, 1249, 1228, 1194, 1171, 1041, 844, 784 and 724; NMR δ$_H$ (400 MHz, CDCl$_3$) 1.24 (3H, d, J 6.5 Hz) 2.60 (2H, m) 2.92 (4H, m) 3.85 (3H, s) 4.03 (2H, t, J 7 Hz) 4.36 (1H, m) 6.37 (1H, d, J 6.5 Hz, NH) 6.79 (1H, dd, J 2.5, 8.5 Hz) 6.96 (1H, d, J 3 Hz) 7.11 (lH, d, J 9 Hz).

Enantiomer 1 and Enantiomer 2 of 1-(7-Methoxy-2, 3-dihydro-1H-pyrrolo[1,2-a]indol-9-yl)-2-(trifluoroacetamido)-propane (RS)-(7-Methoxy-2,3-dihydro-1H-pyrrolo[1,2-a]indol-9-yl)-2-(trifluoroacetamido)-propane (0.10 g, 0.29 mmol) was dissolved in dichloromethane (500 μL) and half of the resultant solution was repeat-loaded onto a Chiralcel OD column (300mm×4.6 mm) [10μL injections; 1.0 mL/min; hexane-2-propanol (90:10); 220 nm] to afford, after removal of solvent, enantiomer 1 of (7-methoxy-2,3-dihydro-1H-pyrrolo[1,2-a]indol-9-yl)-2-(trifluoroacetamido)-propane (0.018 g, 36%) as an off-white solid; LC: [Chiralcel OD; hexane-2-propanol (90:10); 1.0 mL/min; 220 nm] 99.1% (11.59 min) and 0.9% (15.90 min); [Supelcosil ABZ+; methanol-10 mM aqueous ammonium acetate solution (80:20)] 96.4% (3.08 min); and (S or R)-(7-methoxy-2,3-dihydro-1H-pyrrolo[1,2 -a]indol-9-yl)-2-(trifluoroacetamido)-propane (0.018 g, 36%, 92% e.e.) as a pale green solid; LC: [Chiralcel OD; hexane-2-propanol (90:10); 1.0 mL/min; 220 nm] 4.0% (11.47 min) and 96.0% (15.76 min); [Supelcosil ABZ+; methanol-10 mM aqueous ammonium acetate solution (80:20)] 94% (3.09 min).

Enantiomer 1 of 1-(7-Methoxy-2,3-dihydro-1H-pyrrolo[1,2-a]indol-9-yl)-propylamine fumarate To a solution of the first-eluting trifluoroacetamide enantiomer (0.018 g, 0.05 mmol) in methanol (10 mL) was added potassium carbonate (0.02 g, 0.14 mmol) and 5 drops of water, and the resultant suspension was stirred for 18 h. The solvent was removed in vacuo and the residue was dissolved in ethyl acetate, dried (magnesium sulfate), concentrated in vacuo and purified by flash column chromatography [SiO$_2$; ethyl acetate →ethyl acetate-methanol-0.880 ammonia solution (90:8:2)] to afford a colourless oil (0.0055 g). The oil was dissolved in 2-propanol (0.1 mL) and added to a solution of fumaric acid (0.0039 g, 0.034 mmol) in 2-propanol (1 mL) at 50° C. and the mixture was evaporated to a residual amount of solvent. Ether was added, and the mixture was filtered. The filter-cake was washed with cold ether to afford the product (0.0035 g, 43%) as a white solid: LC: [Supelcosil ABZ+; methanol-10 mM aqueous anmmonium acetate solution (70:30)] 94% (1.95 min); LC (sample treated with excess trifluoroacetic anhydride): [Chiralcel OD; hexane-2-propanol (90:10); 1.0 mL/min; 220 nm]>99% (12.28 min); m/z (ES$^+$) 308 [(M+Na+MeCN)$^+$, 5%], 245 (MH$^+$, 7%) and 228 [(MH–NH$_3$)$^+$, 100%].

Enantiomer 2 of 1-(7-Methoxy-2,3-dihydro-1H-pyrrolo[1,2-a]indol-9-yl)-2-propylamine fumarate enantiomer 2 of 1-(7-Methoxy-2,3-dihydro-1H-pyrrolo[1, 2-a]indol-9-yl)-2-propylamine fumarate was prepared from second-eluting trifluoroacetamide enantiomer according to the method described above to give 0.0018 g (25%) of the product as a white solid: LC: [Supelcosil ABZ+; methanol-10 mM aqueous ammonium acetate solution (80:20)] 98% (1.69 min); LC (sample treated with excess trifluoroacetic anhydride): [Chiralcel OD; hexane-2-propanol (90:10); 1.0 mL/min; 220 nm] 1% (12.58 min) and 99% (17.07 min); m/z (ES$_+$) 245 (MH$^+$, 5%) and 228 [(MH–NH$_3$)$^+$, 100%].

Example 10

(RS)-1-(7-Benzyloxy-2,3-dihydro-1H-pyrrolo[1,2-a] indol-9-yl)-2-propylamine fumarate

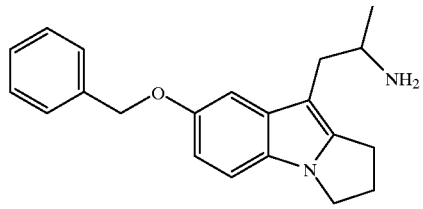

5-Benzyloxyindole-3-carboxaldehyde

5-Benzyloxyindole-3-carboxaldehyde was prepared from 5-benzyloxyindole according to the method described in Example 1 to give the crude product as a pale-brown solid which was used immediately without further purification.

5-Benzyloxy-1-(3-chloropropyl)indole-3-carboxaldehyde

5-Benzyloxy-1-(3-chloropropyl)indole-3-carboxaldehyde was prepared from 5-benzyloxyindole-3-carboxaldehyde according to the method described in Example 1 to give 4.4 g (68% from 5-benzyloxyindole) of the product as brown needles: mp 134–135° C.; IR v$_{max}$ (Nujol)/cm$^{-1}$ 2924, 1655, 1527, 1228, 1036, 787 and 707; NMR δ$_H$ (400 MHz, CDCl$_3$) 2.28 (2H, m), 3.45–3.48 (2H, t, J 5.9 Hz), 4.37 (2H, t, J 6.5 Hz), 513 (2H, s), 7.05 (1H, dd, J 9.1, 2.5 Hz), 7.28–7.48 (6H, m), 7.70 (1H, s), 7.91 (1H, d, J, 2.5 Hz) and 9.96 (1H, s); Found: C, 69.62; H, 5.58; N, 4.30%. C$_{19}$H$_{18}$ClNO$_2$ requires: C, 69.62; H, 5.53; N, 4.27%.

5-Benzyloxy-1-(3-iodopropyl)indole-3-carboxaldehyde

This was prepared from 5-benzyloxy-1-(3-iodopropyl) indole-3-carboxaldehyde according to the method described in Example 1 to give the product as an oil which was used immediately without further purification.

7-Benzyloxy-2,3-dihydro-1H-pyrrolo[1,2-a]indole-9-carboxaldehyde

7-Benzyloxy-2,3-dihydro-1H-pyrrolo[1,2-a]indole-9-carboxaldehyde was prepared from 5-benzyloxy-1-(3-chloropropyl)indole-3-carboxaldehyde according to the method described in Example 1 to give 1.55 g (40%) of the product as an off-white solid: mp 165–166° C.; IR v$_{max}$ (nujol)/cm$^{-1}$; 2925, 1640, 1458, 1228, 1136, 1033 and 723; NMR δ$_H$ (400 MHz, CDCl$_3$) 2.68–2.72 (2H, m), 3.27 (2H, t, J 7.5 Hz), 4.10 (2H, t, J 7.6 Hz), 5.12 (2H, s), 6.92 (1H, d, J 2.6 Hz), 6.95–7.48 (6H, m), 7.82 (1H, s) and 9.89 (1H, s); Found: C, 78.02; H, 5.92; N, 4.70%. C$_{19}$H$_{17}$NO$_2$ requires: C, 78.33; H, 5.88; N, 4.81%.

1-(7-Benzyloxy-2,3-dihydro-1H-pyrrolo[1,2-a]indol-9-yl)-2-nitro-1-propene 1-(7-Benzyloxy-2,3-dihydro-1H-pyrrolo[1,2-a]indol-9-yl)-2-nitro-1-propene was prepared from 7-benzyloxy-2,3- dihydro-1H-pyrrolo[1,2-a]indole-9-carboxaldehyde according to the method described in Example 1 to give 0.71 g (74%) of the product as a dark brown solid: mp 146–147° C. (decomp); IR $v_{max}$ (Nujol)/cm$^{-1}$ 2925, 1626, 1465, 1267, 1208 and 855; NMR $\delta_H$ (400 MHz, CDCl$_3$) 2.37 (3H, s), 2.67–2.70 (2H, m), 3.09 (2H, t, J 7.1 Hz), 4.12 (2H, t, J 7.1 Hz), 5.11 (2H, s), 6.95 (1H, dd, J 8.7, 2.5 Hz), 7.13–7.47 (7H, m) and 8.35 (1H, s); Found: C, 72.17; H, 5.77; N, 7.95%. C$_{21}$H$_{20}$N$_2$O$_3$ requires: C, 72.40; H, 5.79; N, 8.04%.

(RS)-1-(7-Benzyloxy-2,3-dihydro-1H-pyrrolo[1,2-a]indol-9-yl)-2-propylamine fumarate This was prepared from 1-(7-benzyloxy-2,3-dihydro-1H-pyrrolo[1,2-a]indol-9-yl)-2-nitro-1-propene according to the method described in Example 3 to give 0.17g (18%) of the title compound as an off-white solid: mp darkens at 180° C., melts over 188–198° C.; IR $v_{max}$ (Nujol)/cm$^{-1}$ 2923, 1626, 1464, 1222, 736 and 650; NMR $\delta_H$ (400 MHz, DMSO-d$_6$) 1.13 (3H, d, J 6.6 Hz), 2.50–2.56 (2H, m), 2.68–2.74 (1H, m), 2.87–2.96 (3H, m), 3.33–3.39 (1H, m), 3.99 (2H, t, J 7.5 Hz), 5.09 (2H, s), 6.43 (2H, s), 6.74–677 (1H, dd, J 8.6, 2.5 Hz) and 7.15–7.48 (7H, m); Found: C, 67.84; H, 6.37; N, 6.30%. C$_{21}$H$_{24}$N$_2$O.C$_4$H$_4$O$_4$0.5H$_2$O requires: C, 67.40; H, 6.56; N, 6.29%.

Example 11

(RS)-1-(7-Methylthio-2,3-dihydro-1H-pyrrolo[1,2-a]indol-9-yl)-2-propylamine fumarate

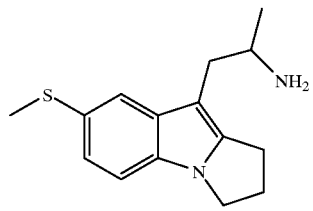

5-Methylthioindole-3-carboxaldehyde

5-Methylthioindole-3-carboxaldehyde was prepared from 5-methylthioindole (Heterocycles, 1992, 34, 1169–1175) according to the method described in Example 1 to give 1.85 g (86%) of the product as a white solid: mp 182–183° C.; IR $v_{max}$ (Nujol)/cm$^{-1}$ 3172, 2926, 2807, 1632, 1440, 1130 and 972; NMR $\delta_H$ (400 MHz, DMSO-d$_6$) 2.50 (3H, s), 7.24 (1H, dd, J 11.4, 2.8 Hz), 7.50 (1H, d, J, 11.5 Hz), 7.96 (1H, s), 8.28 (1H, s) and 9.92 (1H, s).

1-(3-Chloropropyl)-5-methylthio-indole-3-carboxaldehyde 1-(3-Chloropropyl)-5-methylthio-indole-3-carboxaldehyde was prepared from 5-methylthioindole-3-carboxaldehyde according to the method described in Example 1 to give 2.36 g (94%) of the product as a pale-yellow solid: mp 64–65° C.; IR $v_{max}$ (Nujol)/cm$^{-1}$ 2924, 2809, 1656, 1534, 1399, 1172, 1027, 813 and 786; NMR $\delta_H$ (400 MHz, CDCl$_3$) 2.27–2.33 (2H, m), 2.54 (3H, s), 3.46 (2H, t, J 5.7 Hz), 4.38 (2H, t, J 6.5 Hz), 7.29 (2H, s), 7.71 (1H, s), 8.22 (1H, s) and 9.96 (1H, s).

1-(3-Iodopropyl)-5-methylthio-indole-3-carboxaldehyde 1-(3-Iodopropyl)-5-methylthio-indole-3-carboxaldehyde was prepared from 1-(3-chloropropyl)-5-methylthio-indole-3-carboxaldehyde according to the method described in Example 1 to give the product as a pale-brown oil which was used immediately without further purification.

7-Methylthio-2,3-dihydro-1H-pyrrolo[1,2-a]indole-9-carboxaldehyde

7-Methylthio-2,3-dihydro-1H-pyrrolo[1,2-a]indole-9-carboxaldehyde was prepared from 1-(3-iodopropyl)-5-methylthio-indole-3-carboxaldehyde according to the method described in Example 1 to give 0.80 g (40%) of the product as a pale-yellow solid: mp 140–141° C.; IR $v_{max}$ (Nujol)/cm$^{-1}$ 2924, 2724, 1639, 1465, 1029 and 820; NMR $\delta_H$ (400 MHz, CDCl$_3$) 2.53 (3H, s), 2.68–2.76 (2H, m), 3.28 (2H, t, J 7.5), 4.12 (2H, t, J 7.1 Hz), 7.14–7.22 (2H, m), 8.12 (1H, s) and 9.90 (1H, s).

1-(7-Methylthio-2,3-dihydro-1H-pyrrolo[1,2-a]indol-9-yl)-2-nitro-1-propene 1-(7-Methylthio-2,3-dihydro-1H-pyrrolo[1,2-a]indol-9-yl)-2-nitro-1-propene was prepared from 7-methylthio-2,3-dihydro-1H-pyrrolo[1,2-a]indole-9-carboxaldehyde according to the method described in Example 1 to give 0.60 g (80%) of the product as an orange solid: mp 135–136° C.; IR $v_{max}$ (Nujol)/cm$^{-1}$ 2924, 1636, 1475, 1277, 979 and 800; NMR $\delta_H$ (400 MHz, CDCl$_3$) 2.41 (3H, s), 2.52 (3H, s), 2.66–2.70 (2H, m), 3.10 (2H, t, J 7.2 Hz), 4.14 (2H, t, J 7.1 Hz), 7.17–7.23 (2H, m), 7.54 (1H, s) and 8.35 (1H, s).

(RS)-1-(7-Methylthio-2,3-dihydro-1H-pyrrolo[1,2-a]indol-9-yl)-2-propylamine fumarate (RS)-1-(7-Methylthio-2,3-dihydro-1H-pyrrolo[1,2-a]indol-9-yl)-2-propylamine fumarate was prepared from 1-(7-methylthio-2,3-dihydro-1H-pyrrolo[1,2-a]indol-9-yl)-2-nitro-1-propene according to the method described in Example 3 to give 0.23 g (30%) of the title compound as pale-yellow crystals: mp 204–206° C. (dec.); IR $v_{max}$ (Nujol)/cm$^{-1}$ 3052, 2924, 1612, 1463, 1310, 992 and 788; NMR $\delta_H$ (400 MHz, DMSO-d$_6$) 1.14 (3H, d, J 6.1 Hz), 2.46 (3H, s), 2.50–2.55 (2H, m), 2.71–2.76 (1H, m), 2.89–2.99 (3H, m), 3.34–3.36 (1H, m), 4.02 (2H, t, J 7.1 Hz), 6.43 (2H, s), 7.04 (1H, dd, J 8.4, 1.9 Hz), 7.24 (1H, d, J, 8.1 Hz) and 7.50 (1H, d, J 1.4 Hz).

Example 12

(RS) N-(2-Methylpropyl)-1-[(7-methoxy-2,3-dihydro-1H-pyrrolo[1,2-a]indol-9-yl)]-2-propylamine hydrochloride

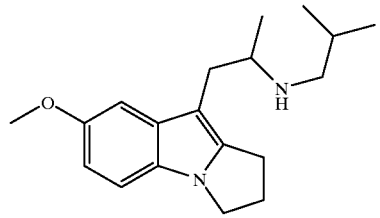

A mixture of (RS)-(7-methoxy-2,3-dihydro-1H-pyrrolo[1,2-a]indol-9-yl)-2-propylamine (0.030 g, 0.12 mmol), 3-methylpropanal (0.021 mL, 0.24 mmol) and methanol (1 mL) was shaken for 3 h. To the mixture was added Amberlite IRA-400 borohydride resin (2.5 mmol/g —BH$_4$, 0.12 g, 0.3 mmol) and the mixture was shaken for 18 h. To the mixture was added PS-benzaldehyde (2.5 mmol/g —CHO, 0.12 g, 0.3 mmol) and the mixture was shaken for 18 h and filtered. The filter-cake was washed with dichloromethane (2×1 mL) and methanol (2×1 mL) and the filtrate was concentrated in vacuo. The concentrate was dissolved in dichloromethane (2 mL) and Amberlyst-15 (0.5 g) was added. The mixture was shaken for 1 h and filtered. The filter-cake was washed with dichloromethane (2×1 mL) and methanol (2×1 mL), suspended in methanolic ammonia solution (2 M, 1 mL, 2 mmol), shaken for 1 h, and filtered. The filter-cake was washed (dichloromethane) and the filtrate was concentrated in vacuo. The concentrate was treated with ethereal hydrogen chloride solution (1 M, 1 mL, 1 mmol) and concentrated in vacuo to give the product as a beige solid (0.02 g, 49%): mp 178–181° C.; NMR $\delta_H$ (400 MHz, DMSO-$d_6$) 1.01 (6H, m) 1.17 (3H, d, J 6.5 Hz) 2.56 (2H, m) 2.77 (1H, m) 2.77 (1H, m) 2.86 (1H, m) 2.93 (2H, m) 3.22 (1H, m) 3.39 (1H, m) 3.51 (1H, m) 3.78 (3H, s) 4.02 (2H, t, J 7 Hz) 6.71 (1H, dd, J 2.5, 8.5 Hz) 7.11 )1H, s) 7.19 (1H, d, J 8.5 Hz).

Example 13

(RS) N-(Cyclopropylmethyl)-1-[(7-methoxy-2,3-dihydro-1H-pyrrolo[1,2-a]indol-9-yl)]-2-propylamine hydrochloride

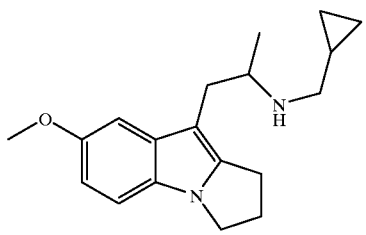

(RS) N-(Cyclopropylmethyl)-1-[(7-methoxy-2,3-dihydro-1H-pyrrolo[1,2-a]indol-9-yl)]-2-propylamine hydrochloride was prepared from (RS)-(7-methoxy-2,3-dihydro-1H-pyrrolo[1,2-a]indol-9-yl)-2-propylamine and cyclopropylcarboxaldehyde according to the method described in Example 12 to give 0.024 g (54%) of the product as a beige solid: mp 149–151° C.; NMR $\delta_H$ (400 MHz, DMSO-$d_6$) 0.41 (2H, dd, J 5, 9 Hz) 0.62 (2H, d, J 9 Hz) 1.15 (3H, d, J 6.5 Hz) 2.56 (2H, m) 2.73 (1H, dd, J 10.5, 14 Hz) 2.93 (6H, m) 3.78 (3H, s) 4.02 (2H, t, J 7 Hz) 6.71 (1H, dd, J 2.5 9 Hz) 7.07 (1H, d, J 2.5 Hz) 7.19 (1H, d, J 9 Hz).

Example 14

(RS) N-(Cyclohexylmethyl)-1-[(7-methoxy-2,3-dihydro-1H-pyrrolo[1,2-a]indol-9-yl)]-2-propylamine hydrochloride

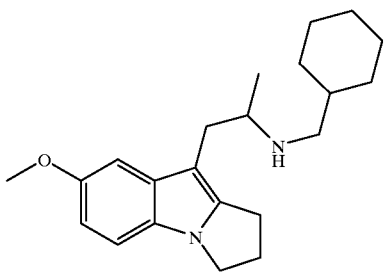

(RS) N-(Cyclohexylmethyl)-1-[(7-methoxy-2,3-dihydro-1H-pyrrolo[1,2-a]indol-9-yl)]-2-propylamine hydrochloride was prepared from (RS)-(7-methoxy-2,3-dihydro-1H-pyrrolo[1,2-a]indol-9-yl)-2-propylamine and cyclohexylcarboxaldehyde according to the method described in Example 12 to give 0.023 g (50%) of the product as a beige solid: mp 210–3° C.; NMR $\delta_H$ (400 MHz, DMSO-$d_6$) 1.01 (2H, m) 1.17 (3H, d, J 6.5 Hz) 1.22 (3H, m) 1.73 (6H, m) 2.55 (2H, m) 2.77 (1H, m) 2.84 (2H, m) 2.93 (2H, m) 3.24 (1H, m) 3.39 (1H, m) 3.78 (3H, s) 4.02 (2H, t, J 7 Hz) 6.70 (1H, dd J 2.5, 8.5 Hz) 7.13 (1H, d, J 2.5 Hz) 7.18 (1H, d, J 8.5 Hz).

Example 15

(RS) N-(2,2-Dimethylpropyl)-1-[(7-methoxy-2,3-dihydro-1H-pyrrolo[1,2-a]indol-9-yl)]-2-propylamine hydrochloride

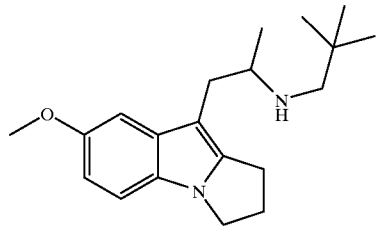

(RS) N-(2,2-Dimethylpropyl)-1-[(7-methoxy-2,3-dihydro-1H-pyrrolo[1,2-a]indol-9-yl)]-2-propylamine hydrochloride was prepared from from (RS)-(7-methoxy-2,3-dihydro-1H-pyrrolo[1,2-a]indol-9-yl)-2-propylamine and 2,2-dimethylpropionaldehyde according to the method described in Example 12 to give 0.030 g (70%) of the product as a beige solid: mp 226–228° C.; NMR $\delta_H$ (400 MHz, DMSO-$d_6$) 1.07 (9H, s) 1.17 (3H, d, J 6.5 Hz) 2.56 (2H, m) 2.65 (2H, m) 2.80 (1H, dd, J 11.5, 13.5 Hz) 2.89 (2H, t, J 6.5 Hz) 2.94 (1H, m) 3.25 (1H, m) 3.79 (3H, s) 4.02 (2H, t, J 7 Hz) 6.71 (1H, dd, J 2.5 8.5 Hz) 7.17 (1H, s) 7.20 (1H, d, J 8.5 Hz).

Example 16

(RS) N-(3-Methylbutyl)-1-(7-methoxy-2,3-dihydro-1H-pyrrolo[1,2-a]indol-9-yl)]-2-propylamine hydrochloride

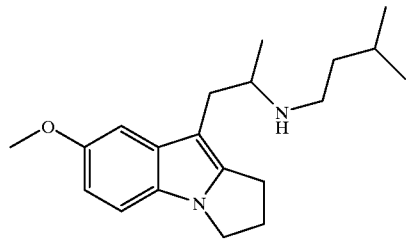

(RS) N-(3-Methylbutyl)-1-(7-methoxy-2,3-dihydro-1H-pyrrolo[1,2-a]indol-9-yl)]-2-propylamine hydrochloride was prepared from from (RS)-(7-methoxy-2,3-dihydro-1H-pyrrolo[1,2-a]indol-9-yl)-2-propylamine and 3-methylbutyraldehyde according to the method described in Example 12 to give 0.016 g (38%) of the product as a beige solid: mp 118–121° C.; NMR $\delta_H$ (400 MHz, DMSO-$d_6$) 0.92 (6H, d, J 14.5 Hz) 1.17 (3H, d, J 6.5 Hz) 1.55 (2H, m) 1.67 (2H, m) 2.55 (2H, m) 2.74 (1H, dd, J 10, 14 Hz) 2.94 (2H, m) 2.97 (2H, m) 3.19 (1H, dd, J, 4, 14 Hz) 3.78 (3H, s) 4.02 (2H, t, J 7 Hz) 6.71 (1H, dd J 2.5, 8.5 Hz) 7.08 (1H, d, J 2.5 Hz) 7.19 (1H, d, J 8.5 Hz).

Example 17

(RS)-1-(2-Methoxy-6,7,8,9-tetrahydro-pyrido[1,2-a]
indol-10-yl)-2-propylamine fumarate

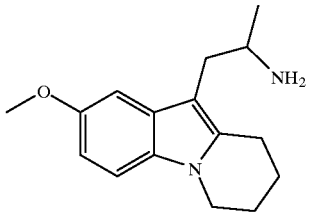

5-Methoxyindole-3-carboxaldehyde

To stirred dimethylformamide is added dropwise phosphorus oxychloride. The mixture is stirred for 10 min and a solution of 5-methoxyindole in dimethylformamide is added dropwise. The mixture is heated to 40° C. for 45 min, cooled to room temperature and then treated with a solution of sodium hydroxide in water. The mixture is heated to 50° C. for 10 min, cooled to room temperature, poured onto crushed ice and filtered. The filter cake is recrystallised (methanol) to give the product as a white solid.

5-Methoxy-1-(4-chlorobutyl)indole-3-carboxaldehyde

To a stirred mixture of powdered potassium hydroxide in methyl sulfoxide is added dropwise a solution of 5-methoxyindole-3-carboxaldehyde in methyl sulfoxide. The mixture is stirred for 30 min and 1-bromo-4-chlorobutane is added dropwise. The mixture is stirred for 1 h and partitioned between ethyl acetate and water. The combined organic extracts are washed (water, brine), dried (sodium sulfate) and concentrated in vacuo to give the product.

5-Methoxy-1-(4-iodobutyl)indole-3-carboxaldehyde

A stirred solution of 5-methoxy-1-(4-chlorobutyl)indole-3-carboxaldehyde and sodium iodide in acetonitrile under argon is heated under reflux for 18 h, cooled to room temperature and partitioned between ether and water. The combined organic extracts are washed (aqueous sodium metabisulfite solution, water, brine), dried (sodium sulfate) and concentrated in vacuo to give the product.

2-Methoxy-6,7,8,9-tetrahydro-pyrido[1,2-a]indole-10-carboxaldehyde

To a stirred solution of 5-methoxy-1-(4-iodobutyl)indole-3-carboxaldehyde in toluene at reflux under argon is added dropwise over 2 h a solution of 1,1'-azobis(cyclohexanecarbonitrile) and tri-n-butyltin hydride in toluene. The mixture is stirred for 3 h, cooled to room temperature, and potassium fluoride and water are added. The mixture is stirred for 18 h and filtered through a pad of kieselguhr. The filter-cake is washed (ethyl acetate) and the filtrate is concentrated in vacuo and purified by column chromatography to give the product.

1-(2-Methoxy-6,7,8,9-tetrahydro-pyrido[1,2-a]indol-10-yl)-2-nitro-1-propene A stirred solution of 2-methoxy-6,7,8,9-tetrahydro-pyrido[1,2-a]indole-10-carboxaldehyde and ammonium acetate in nitroethane is heated to 100° C. for 1 h, cooled to room temperature and partitioned between ethyl acetate and water. The combined organic extracts are washed (water, brine), dried (sodium sulfate) and concentrated in vacuo to give the product.

(RS)-1-(2-Methoxy-6,7,8,9-Tetrahydro-pyrido[1,2-a]indol-10-yl)-2-propylamine fumarate To a stirred solution of lithium aluminium hydride in tetrahydrofuran under argon is added dropwise a solution of 1-(2-methoxy-6,7,8,9-tetrahydro-1H-pyrido[1,2-a]indol-10-yl)-2-nitro-1-propene in tetrahydrofuran. The mixture is heated under reflux for 4 h and cooled to 0° C. To the mixture is added dropwise aqueous potassium sodium tartrate solution and the mixture is stirred for 30 min and filtered through kieselguhr. The filtrate is extracted with dichloromethane. The combined organic extracts are washed (water, brine), dried (sodium sulfate), concentrated in vacuo, dissolved in hot 2-propanol and added dropwise to a stirred solution of fumaric acid in 2-propanol at 50° C. The mixture is cooled to 0° C. and filtered. The filter-cake is washed (2-propanol, ether) and dried to give the product.

Example 18

(RS)-1-(2-Methoxy-7,8,9,10-tetrahydro-6H-azepino
[1,2-a]indol-11-yl)-2-propylamine fumarate

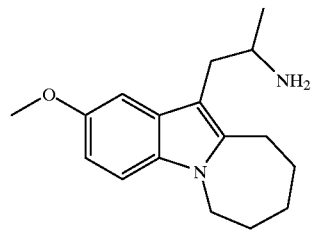

5-Methoxyindole-3-carboxaldehyde

To stirred dimethylformamide is added dropwise phosphorus oxychloride. The mixture is stirred for 10 min and a solution of 5-methoxyindole in dimethylformamide is added dropwise. The mixture is heated to 40° C. for 45 min, cooled to room temperature and then treated with a solution of sodium hydroxide in water. The mixture is heated to 50° C. for 10 min, cooled to room temperature, poured onto crushed ice and filtered. The filter cake is recrystallised (methanol) to give the product as a white solid.

5-Methoxy-1-(5-chloropentyl)indole-3-carboxaldehyde

To a stirred mixture of powdered potassium hydroxide in methyl sulfoxide is added dropwise a solution of 5-methoxyindole-3-carboxaldehyde in methyl sulfoxide. The mixture is stirred for 30 min and 1-bromo-5-chloropentane is added dropwise. The mixture is stirred for 1 h and partitioned between ethyl acetate and water. The combined organic extracts are washed (water, brine), dried (sodium sulfate) and concentrated in vacuo to give the product.

5-Methoxy-1-(5-iodopentyl)indole-3-carboxaldehyde

A stirred solution of 5-methoxy-1-(5-chloropentyl)indole-3-carboxaldehyde and sodium iodide in acetonitrile under argon is heated under reflux for 18 h, cooled to room temperature and partitioned between ether and water. The combined organic extracts are washed (aqueous sodium metabisulfite solution, water, brine), dried (sodium sulfate) and concentrated in vacuo to give the product.

2-Methoxy-7,8,9,10-tetrahydro-6H-azepino[1,2-a] indole-11-carboxaldehyde

To a stirred solution of 5-methoxy-1-(5-iodopentyl) indole-3-carboxaldehyde in toluene at reflux under argon is added dropwise over 2 h a solution of 1,1'-azobis (cyclohexanecarbonitrile) and tri-n-butyltin hydride in toluene. The mixture is stirred for 3 h, cooled to room temperature, and potassium fluoride and water are added. The mixture is stirred for 18 h and filtered through a pad of kieselguhr. The filter-cake is washed (ethyl acetate) and the filtrate is concentrated in vacuo and purified by column chromatography to give the product.

1-(2-Methoxy-7,8,9,10-tetrahydro-6H-azepino[1,2-a] indol 11-yl)-2-nitro-1-propene A stirred solution of 2-methoxy-7,8,9,10-tetrahydro-6H-azepino[1,2-a]indole-11-carboxaldehyde and ammonium acetate in nitroethane is heated to 100° C. for 1 h, cooled to room temperature and partitioned between ethyl acetate and water. The combined organic extracts are washed (water, brine), dried (sodium sulfate) and concentrated in vacuo to give the product.

(RS)-1-(2-Methoxy-7,8,9,10-tetrahydro-6H-azepino [1,2-a]indol-11-yl)-2-propylamine fumarate To a stirred solution of lithium aluminium hydride in tetrahydrofuran under argon is added dropwise a solution of 1-(2-methoxy-7,8,9,10-tetrahydro-6H-azepino[1,2-a]indol-11-yl)-2-nitro-1-propene in tetrahydrofuran. The mixture is heated under reflux for 4 h and cooled to 0° C. To the mixture is added dropwise aqueous potassium sodium tartrate solution and the mixture is stirred for 30 min and filtered through kieselguhr. The filtrate is extracted with dichloromethane. The combined organic extracts are washed (water, brine), dried (sodium sulfate), concentrated in vacuo, dissolved in hot 2-propanol and added dropwise to a stirred solution of fumaric acid in 2-propanol at 50° C. The mixture is cooled to 0° C. and filtered. The filter-cake is washed (2-propanol, ether) and dried to give the product.

What is claimed is:

1. A chemical compound of formula (I):

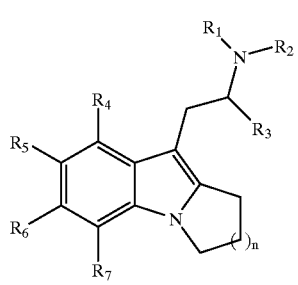

(I)

wherein:
n is 1, 2 or 3;
$R_1$ and $R_2$ are independently selected from hydrogen and alkyl;
$R_3$ is alkyl;
$R_4$ to $R_7$ are independently selected from hydrogen, halogen, hydroxy, alkyl, aryl, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, or $R_5$ and $R_6$ together form a carbocyclic or heterocyclic ring, or pharmaceutically acceptable salts thereof.

2. A compound according to claim 1 wherein n=1.

3. A compound according to claim 1 wherein $R_1$ and $R_2$ are hydrogen.

4. A compound according to claim 1 wherein $R_1$ is hydrogen and $R_2$ is alkyl.

5. A compound according to claim 1 wherein $R_1$ is hydrogen and $R_2$ is arylalkyl.

6. A compound according to claim 1 wherein $R_3$ is methyl.

7. A compound according to claim 1 wherein $R_4$ to $R_7$ are selected the group consisting of hydrogen, halogen, hydroxy, alkyl, aryl, alkoxy, aryloxy, alkylthio, alkylsulfoxyl and alkylsulfonyl.

8. A compound according to claim 1 wherein $R_4$ is hydrogen or halogen.

9. A claim according to claim 1 wherein $R_5$ is other than hydrogen.

10. A compound according to claim 1 wherein $R_5$ is selected from halogen, alkyl, alkoxy and alkylthio.

11. A compound according to claim 1 wherein $R_6$ is other than hydrogen.

12. A compound according to claim 1 wherein $R_6$ is selected from hydrogen and halogen.

13. A compound according to claim 1 wherein $R_5$ and $R_6$ together form an O, S or N containing heterocyclic ring.

14. A compound according to claim 13 wherein said ring is a 5-or 6-membered ring.

15. A compound according to any claim 1 wherein $R_7$ is hydrogen.

16. A compound according to claim 1 wherein two or three of $R_4$, $R_5$, $R_6$ and $R_7$ are hydrogen.

17. A compound according to claim 1 wherein the compounds of formula (I) are selected the group consisting of 1-(7-chloro-2,3-dihydro-1H-pyrrolo[1,2-a]indol-9-yl)-2-propylamine, 1-(6,7-difluoro-2,3-dihydro-1H-pyrrolo[1,2-a]indol-9-yl)-2-propylamine, 1-(7-bromo-2,3-dihydro-1H-pyrrolo[1,2-a]indol-9-yl)-2-propylamine, 1-(7-methoxy-2,3-dihydro-1H-pyrrolo[1,2-a]indol-9-yl)-2-propylamine and 1-(7-methylthio-2,3-dihydro-1H-pyrrolo[1,2-a]indol-9-yl)-2-propylamine.

18. A compound according to claim 1 which is the (S)-enantiomer thereof.

19. A method of treatment of disorders of the central nervous system; damage to the central nervous system; cardiovascular disorders; gastrointestinal disorders; diabetes insipidus, and sleep apnea comprising administering to a patient in need of such treatment an effective dose of a compound of formula (I) as set out in claim 1.

20. A method according to claim 19 wherein the disorders of the central nervous system are selected the group consisting of depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension.

21. A method according to claim 20 wherein the damage to the central nervous system is by trauma, stroke, neurodegenerative diseases or toxic or infective CNS diseases.

22. A method according to claim 21 wherein said toxic or infective CNS disease is encephalitis or meningitis.

23. A method according to claim 19 wherein the cardiovascular disorder is thrombosis.

24. A method according to claim 19 wherein the gastrointestinal disorder is dysfunction of gastrointestinal motility.

25. A method according to claim 19 wherein said medicament is for the treatment of obesity.

26. A method according to claim 19 wherein said treatment is prophylactic treatment.

27. A pharmaceutical composition comprising a compound of formula (I) as set out in claim 1 in combination with a pharmaceutically acceptable carrier or excipient.

* * * * *